(12) United States Patent
Accisano, III et al.

(10) Patent No.: US 7,641,630 B2
(45) Date of Patent: Jan. 5, 2010

(54) DRAINAGE CATHETER HUB WITH LOCKING CAM

(75) Inventors: Nicholas Gerald Accisano, III, Howell, NJ (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 566 days.

(21) Appl. No.: 11/078,140

(22) Filed: Mar. 11, 2005

(65) Prior Publication Data

US 2006/0217667 A1   Sep. 28, 2006

(51) Int. Cl.
*A61M 31/00* (2006.01)
*A61M 37/00* (2006.01)
*A61M 5/178* (2006.01)
*A61B 5/00* (2006.01)

(52) U.S. Cl. ............ 604/95.04; 604/164.1; 604/164.02; 600/585

(58) Field of Classification Search ................ 606/153, 606/151, 232, 139, 144, 155; 604/95.04, 604/104, 95.01, 106, 107, 180, 523, 35, 533, 604/175, 264, 506, 516, 174, 170.01, 540, 604/9

See application file for complete search history.

(56) References Cited

U.S. PATENT DOCUMENTS

| | | | |
|---|---|---|---|
| 1,207,479 A | 12/1916 | Bisgaard | |
| 3,315,592 A * | 4/1967 | Lems | 100/3 |
| 3,513,848 A | 5/1970 | Winston et al. | |
| 3,798,687 A * | 3/1974 | Stevens | 7/129 |
| 3,924,633 A | 12/1975 | Cook et al. | |
| 4,206,910 A | 6/1980 | Biesemeyer | |
| 4,573,981 A | 3/1986 | McFarlane | |
| 4,586,923 A | 5/1986 | Gould et al. | |
| 4,643,720 A | 2/1987 | Lanciano | |
| 4,738,667 A | 4/1988 | Galloway | |
| 4,740,195 A * | 4/1988 | Lanciano | 604/533 |
| 4,787,892 A | 11/1988 | Rosenberg | |
| 4,885,503 A | 12/1989 | Takahashi et al. | |
| 5,052,998 A | 10/1991 | Zimmon | |

(Continued)

FOREIGN PATENT DOCUMENTS

WO    WO 2006/098818    9/2006

(Continued)

OTHER PUBLICATIONS

International Search Report, PCT/US06/03464, mailed Jul. 26, 2007, 2 pgs.

(Continued)

*Primary Examiner*—Nicholas D Lucchesi
*Assistant Examiner*—Ian K Holloway
(74) *Attorney, Agent, or Firm*—Ryan D. Benson; Stoel Rives LLP

(57) ABSTRACT

The drainage catheter hub includes a locking cam for securing a suture to maintain an anchor configuration of the distal end of the drainage catheter. The locking cam is rotatable to a first position for securing the suture and a second position for releasing the suture. The locking cam includes a tapered surface which includes a release portion and a securement portion. The release portion allows movement of the suture while the securement portion cooperatively engages the suture in connection with the seat to minimize movement of the suture.

29 Claims, 6 Drawing Sheets

U.S. PATENT DOCUMENTS

| | | | |
|---|---|---|---|
| 5,074,484 A | 12/1991 | Kray | |
| 5,078,684 A | 1/1992 | Yasuda | |
| 5,213,575 A | 5/1993 | Scotti | |
| 5,308,318 A | 5/1994 | Plassche, Jr. | |
| 5,352,198 A | 10/1994 | Goldenberg et al. | |
| 5,399,165 A | 3/1995 | Paul, Jr. | |
| 5,419,764 A | 5/1995 | Roll | |
| 5,472,435 A | 12/1995 | Sutton | |
| 5,489,269 A | 2/1996 | Aldrich et al. | |
| 5,522,400 A | 6/1996 | Williams | |
| 5,549,331 A | 8/1996 | Yun et al. | |
| 5,666,970 A | 9/1997 | Smith | |
| 5,693,083 A | 12/1997 | Baker et al. | |
| 5,704,926 A | 1/1998 | Sutton | |
| 5,730,724 A * | 3/1998 | Plishka et al. | 604/95.04 |
| 5,806,202 A | 9/1998 | Blackman et al. | |
| 5,893,880 A | 4/1999 | Egan et al. | |
| 5,904,648 A * | 5/1999 | Arndt et al. | 600/120 |
| 6,159,177 A | 12/2000 | Amos et al. | |
| 6,165,183 A | 12/2000 | Kuehn et al. | |
| 6,231,542 B1 * | 5/2001 | Amos et al. | 604/95.01 |
| 6,358,271 B1 | 3/2002 | Egan et al. | |
| 6,454,740 B1 | 9/2002 | Mody | |
| 6,508,789 B1 | 1/2003 | Sinnott et al. | |
| 6,547,761 B2 | 4/2003 | Liu | |
| 6,673,060 B1 | 1/2004 | Fleming, III | |
| 6,699,233 B2 | 3/2004 | Slanda et al. | |
| 7,087,038 B2 | 8/2006 | Lee | |
| 7,217,256 B2 | 5/2007 | Di Palma | |
| 7,578,814 B2 | 8/2009 | Accisano et al. | |
| 2004/0059293 A1 | 3/2004 | Chu et al. | |
| 2005/0070821 A1 | 3/2005 | Deal et al. | |
| 2005/0107739 A1 | 5/2005 | Palma | |
| 2005/0203485 A1 | 9/2005 | Lee | |
| 2006/0206096 A1 | 9/2006 | Accisano et al. | |
| 2006/0212009 A1 | 9/2006 | Accisano et al. | |
| 2007/0032779 A1 | 2/2007 | Accisano et al. | |
| 2007/0083189 A1 | 4/2007 | Lampropoulos | |
| 2008/0097394 A1 | 4/2008 | Lampropoulos | |

FOREIGN PATENT DOCUMENTS

| | | |
|---|---|---|
| WO | WO 2006/098819 | 9/2006 |
| WO | WO 2006/101592 | 9/2006 |
| WO | WO 2007/019074 | 2/2007 |

OTHER PUBLICATIONS

Written Opinion, PCT/US06/03464, mailed Jul. 26, 2007, 2 pgs., 5 pgs.
Angiodynamics, Abscession Drainage Catheter: A Quick Guide to the Locking Mechanism, AngioDynamics, Inc., Nov. 1999.
International Search Report and Written Opinion, PCT/US06/03021, mailed Sep. 18, 2007, Accisano et al.
International Search Report and Written Opinion, PCT/US06/03467, mailed Jun. 14, 2006, Accisano et al.
International Search Report and Written Opinion, PCT/US06/29304, mailed Feb. 21, 2007, Accisano et al.
Office Action issued Sep. 4, 2008 in co-pending U.S. Appl. No. 11/198,642.
Amendment and Response filed Dec. 19, 2008 in co-pending U.S. Appl. No. 11/198,642.
Interview Summary issued Dec. 23, 2008 in co-pending U.S. Appl. No. 11/198,642.
Statement of Substance of Interview filed Jan. 23, 2009 in co-pending U.S. Appl. No. 11/198,642.
Notice of Allowance issued Apr. 20, 2009 in co-pending U.S. Appl. No. 11/198,642.
Issue Notification issued Aug. 5, 2009 in co-pending U.S. Appl. No. 11/198,642.
Request for Continued Examination filed Aug. 24, 2009 in co-pending U.S. Appl. No. 11/198,642.
Final Office Action issued Mar. 10, 2009 in co-pending U.S. Appl. No. 11/081,301.
Amendment and Response filed Dec. 29, 2008 in co-pending U.S. Appl. No. 11/081,301.
Office Action issued Jun. 26, 2008 in co-pending U.S. Appl. No. 11/081,301.
Amendment filed Apr. 23, 2008 in co-pending U.S. Appl. No. 11/081,301.
Office Action issued Oct. 23, 2007 in co-pending U.S. Appl. No. 11/081,301.
Office Action issued Oct. 16, 2008 in co-pending U.S. Appl. No. 11/608,518.
Interview Summary issued Mar. 31, 2009 in co-pending U.S. Appl. No. 11/608,518.
Amendment and Response filed Apr. 16, 2009 in co-pending U.S. Appl. No. 11/608,518.
Notice of Allowance issued Jul. 27, 2009 in co-pending U.S. Appl. No. 11/608,518.
Notice of Allowance issued Aug. 5, 2009 in co-pending U.S. Appl. No. 11/078,939.
Amendment and Response filed Mar. 20, 2009 in co-pending U.S. Appl. No. 11/078,939.
Notice of Non-Compliant Amendment issued Jan. 12, 2009 in co-pending U.S. Appl. No. 11/078,939.
Statement of Substance of Interview filed Jan. 2, 2009 in co-pending U.S. Appl. No. 11/078,939.
Interview Summary issued Dec. 2, 2008 in co-pending U.S. Appl. No. 11/078,939.
Proposed Amendments filed Nov. 21, 2008 in co-pending U.S. Appl. No. 11/078,939.
Office Action issued May 21, 2008 in co-pending U.S. Appl. No. 11/078,939.
Office Action issued May 6, 2009 in co-pending U.S. Appl. No. 11/507,777.
Interview Summary issued Jul. 17, 2009 in co-pending U.S. Appl. No. 11/507,777.
Amendment and Response filed Aug. 6, 2009 in co-pending U.S. Appl. No. 11/507,777.

* cited by examiner

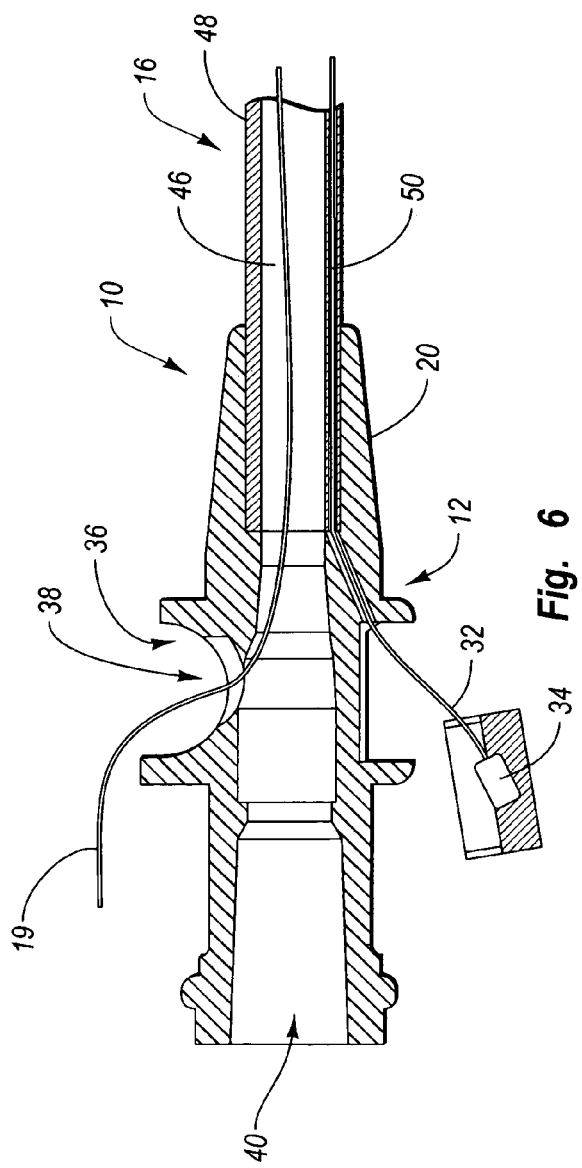
Fig. 6
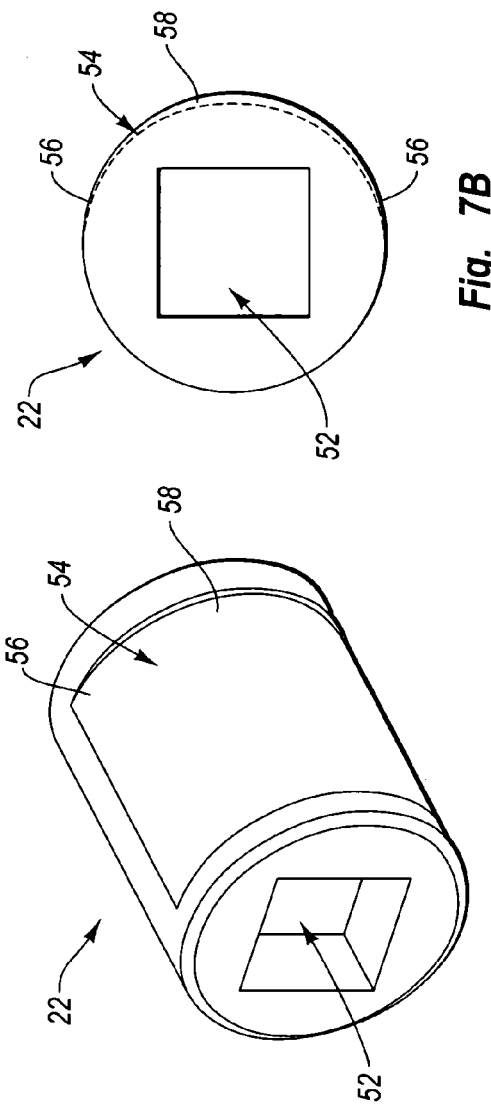
Fig. 7A
Fig. 7B

DRAINAGE CATHETER HUB WITH LOCKING CAM

BACKGROUND OF THE INVENTION

1. The Field of the Invention

The present invention relates to drainage catheters. More particularly, the present invention relates to a drainage catheter hub having a locking cam for securing a suture thread to maintain an anchor configuration of the distal end of the catheter and securing the position of the catheter within the patient's body.

2. The Relevant Technology

One problem often encountered in modern medicines relates to volumes of fluids that collect in a patient's tissue, body cavities, or other positions within the patient's body and that exceed normal volumes. Collected fluids can contribute to infection, exert harmful pressure on the patient's organs, or otherwise impede in proper care and recovery of a patient. Drainage catheters have long been utilized to drain such excess volumes of fluids from patient's body. Typically, the catheter is adapted to be introduced into the patient to the site where the excess fluid is accumulated. A plurality of drainage bores are positioned in the distal end of the drainage catheter to allow passage of the fluids and any materials suspended in the fluids from the volume to the drainage bore of the catheter.

The distal end of drainage catheters are typically adapted to form an anchor configuration to secure the drainage catheter in the site where the excess fluid is accumulated. However, the tissue surrounding drainage sites often does not provide a solid or reliable substrate to maintain the position of the catheter. Additionally, drainage catheter tubes are often formed from a soft resilient material that is easily deformed when pressure is exerted on the tube. As a result, the anchor configuration of the catheter is typically formed in a relatively large pigtail-type loop that provides a reliable anchor regardless of the material properties of the catheter tube and the characteristics of the surrounding tissue. The pigtail loop is formed by curling the tip of the catheter tube until it contacts a proximal position on the catheter tube. This is accomplished utilizing a suture that is threaded between the proximal position and the tip of the catheter. When the suture is foreshortened, the tip of the catheter is securely positioned relative to the proximal position on the catheter tube.

The suture is adapted to run the length of the catheter and exit at the proximal end of the catheter tube. This configuration allows the user to manipulate the suture to maintain or release the anchor configuration of the distal end of the catheter while the distal end of the catheter is positioned inside the patient. Once the anchor configuration of the distal end of the catheter has been established, the practitioner secures the suture to maintain the anchor configuration of the catheter. Otherwise, inadvertent movement of the patient could pull the suture resulting in separation between the tip of the catheter and the proximal position on the catheter tube. In conventional designs, a practitioner wraps or ties the free end of the suture around the proximal portion of the catheter or proximally positioned catheter hub. However, wrapping or tying of the suture can be somewhat inconvenient to perform. Additionally, unwrapping or untying the suture can be difficult when preparing to reposition the anchor or withdraw the drainage catheter from the patient.

A number of devices have been developed to attempt to secure the suture to maintain the anchor configuration the distal end of the drainage catheter. One device provides a catheter hub having a proximal portion and a distal portion which clamp the suture when pushed together. A number of deficiencies are presented by currently available suture securement devices. Many such devices are difficult to manipulate while manually maintaining tension on the suture thread. Additionally, such devices may provide ease in securing the suture, but are not as easily released to allow subsequent manipulation of the suture. Other devices are not intuitive to practitioners utilizing the devices which can require training or lead to improper usage of the device. Some devices do not effectively secure the suture leading to slippage or undesirable placement of the distal end of the catheter within the patient.

BRIEF SUMMARY OF THE INVENTION

The present invention relates to drainage catheters. More particularly, the present invention relates to a drainage catheter hub having a locking cam for securing a suture thread to maintain an anchor configuration of the distal end of the catheter to secure the position of the catheter within the patient's body. The locking cam is adapted to maintain the anchor configuration of the distal end of the catheter. The locking cam is rotatable to a first position to secure the suture and rotatable to a second position to release the suture. The locking cam provides a simple, effective, and easy to understand mechanism for securing the suture. The practitioner positions the distal end of the catheter in a desired position within a patient's body and manually adjusts the suture to create the desired anchor configuration of the distal end of the catheter. The practitioner can then rotate the cam mechanism to a first position to secure the tension on the suture in order to maintain the anchor configuration of the distal end of the catheter. To release the anchor configuration of the distal end of the catheter, the practitioner rotates the cam mechanism to a second position which releases the suture. Releasing the suture allows movement of the suture and provides separation between the tip of the catheter and the proximal portion of the distal end of the catheter.

In one embodiment, a locking tool is provided for use in connection with the locking cam. The locking tool mates with the locking cam in a male/female relationship to provide rotational movement of the locking cam. In one illustrative embodiment, the locking tool provides the male member and the locking cam includes the female component. Placing the female component on the locking cam minimizes inadvertent or unintended movement of the locking cam during use of the drainage catheter. In another embodiment, the locking tool includes a cutting member for trimming the length of suture or severing the catheter tube from the catheter hub when a procedure has been completed.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 6 is a cross-sectional view of the hub body and catheter tube illustrating the juxtaposition of the suture relative to other components of the drainage catheter.

FIG. 7A is a perspective view of the locking cam illustrating the manner in which the locking cam secures the suture relative to the hub body.

FIG. 7B is an end view of the locking cam illustrating the relief surface of the camming portion of the locking cam in phantom lines relative to the outer circumference of the locking cam.

DETAILED DESCRIPTION OF THE PREFERRED EMBODIMENTS

The present invention relates to a drainage catheter hub for use with a drainage catheter. The drainage catheter hub includes a locking cam for securing a suture to maintain an anchor configuration of the distal end of the drainage catheter. The locking cam is rotatable to a first position for securing the suture. The locking cam is also rotatable to a second position for releasing the suture. The locking cam provides a simple, efficient, and easy-to-understand mechanism for selectively securing the suture to maintain the anchor configuration of the distal end of the catheter. In one embodiment the locking cam includes a tapered surface which extends inwardly from the outside diameter of the locking cam. The tapered surface includes a release portion and a securement portion. When the locking cam is rotated such that the suture is positioned between the release portion and the seat in which the locking cam is positioned, movement of the suture is permitted. When the locking cam is rotated such that the suture is positioned between the securement portion and the seat, the suture is cooperatively engaged between the securement portion and the seat and movement of the suture is minimized.

Figure 1:
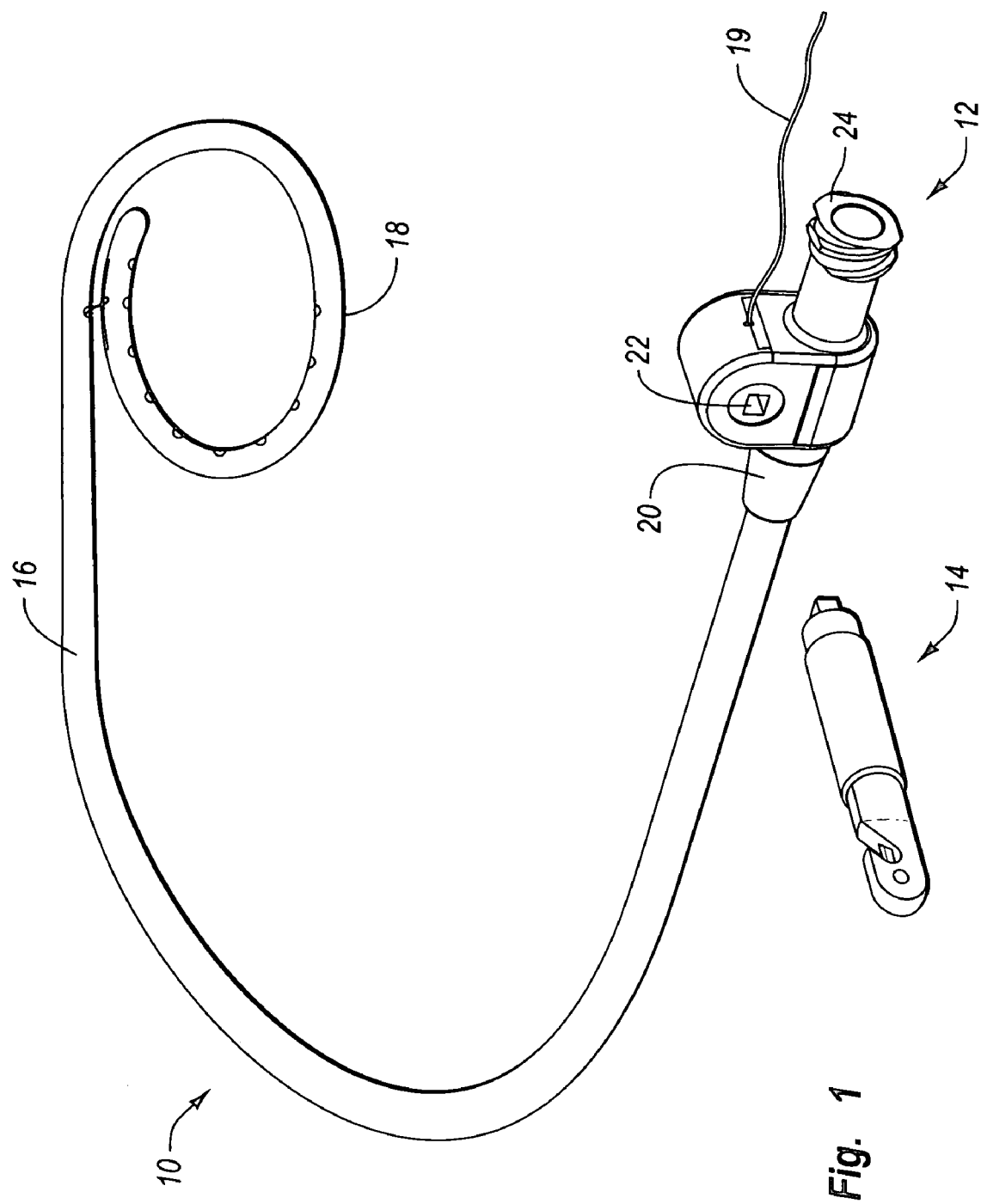
FIG. 1 is a perspective view of a drainage catheter including a catheter hub having a locking cam.

FIG. 1 is a perspective view of a drainage catheter 10 having a drainage as catheter hub 12 positioned at the proximal end of the drainage catheter 10 according to one aspect of the present invention. In the illustrated embodiment, a locking tool 14 is provided in connection with the drainage catheter 10 to facilitate operation of catheter hub 12. Catheter hub 12 is coupled to a catheter tube 16 of drainage catheter 10. Catheter hub 12 is adapted to maintain the anchor configuration of a distal end 18 of catheter tube 16 by securing suture 19. Securing of suture 19 maintains the tension of suture 19 to maintain the position of the tip of the distal end 18 relative to the proximal portion of distal end 18 through which suture 19 is threaded.

In the illustrated embodiment, catheter hub 12 comprises a catheter tube connector 20, a locking cam 22, and a luer coupler 24. Catheter tube connector 20 is positioned at the distal end of catheter hub 12. Catheter tube connector 20 secures catheter tube 16 to catheter hub 12. In the illustrated embodiment, catheter tube connector 20 is insert molded to the catheter tube 16. As will be appreciated by those skilled in the art, a variety of types and configurations of mechanisms for securing the catheter tube to the catheter hub can be utilized without departing from the scope and spirit of the present invention. For example, in one embodiment, the catheter tube is secured to the catheter hub utilizing a compression fitting. In another embodiment, the catheter tube is secured to the catheter hub utilizing a threaded coupler arrangement.

Luer coupler 24 is positioned at the proximal end of catheter hub 12. Luer coupler 24 provides an outlet for drainage catheter 10 to allow the passage of fluid and materials being drained from the patient. Luer coupler 24 allows drainage catheter 10 to be coupled to tubing or a reservoir for containing the fluids being drained from the patient. As will be appreciated by those skilled in the art, a variety of types and configurations of mechanisms for securing the catheter hub to an apparatus for containing fluids being drained from the patient can be utilized without departing from the scope and spirit of the present invention. For example, in one embodiment, a compression fitting is utilized at the proximal end of the catheter.

In the illustrated embodiment, locking cam 22 is positioned between the proximal and distal ends of catheter hub 12. Locking cam 22 is adapted to maintain the anchor configuration of distal end 18 of catheter tube 16. Locking cam 22 is rotatable to a first position to secure suture 19 and rotatable to a second position to release suture 19. Locking cam 22 provides a simple, effective, and easy-to-understand mechanism for securing the suture. In one embodiment, a locking tool is provided for use in connection with the locking cam.

In the illustrated embodiment, a square shaped female member is provided on locking cam 22. Locking tool 14 mates with the female member of locking cam 22 to provide rotational movement of locking cam 22. By utilizing a female member on locking cam 22, there is no projection or surface which can be contacted by the patient, clothing, or other surface that could cause inadvertent movement of locking cam 22. This minimizes the possibility that locking cam 22 can unintentionally secure or release suture 19 at an inopportune or undesired moment during the catheter placement procedure or during operation of drainage catheter 10.

As will be appreciated by those skilled in the art, a variety of types and configurations of mechanisms can be utilized to provide rotational movement of locking cam 22. For example, in one embodiment, locking tool 14 provides the male member and locking cam 22 includes the female component. In another embodiment, locking tool 22 includes a cutting member for trimming the length of suture 19 or severing the catheter tube 16 from the catheter hub 12 when a procedure has been completed.

Figure 2:
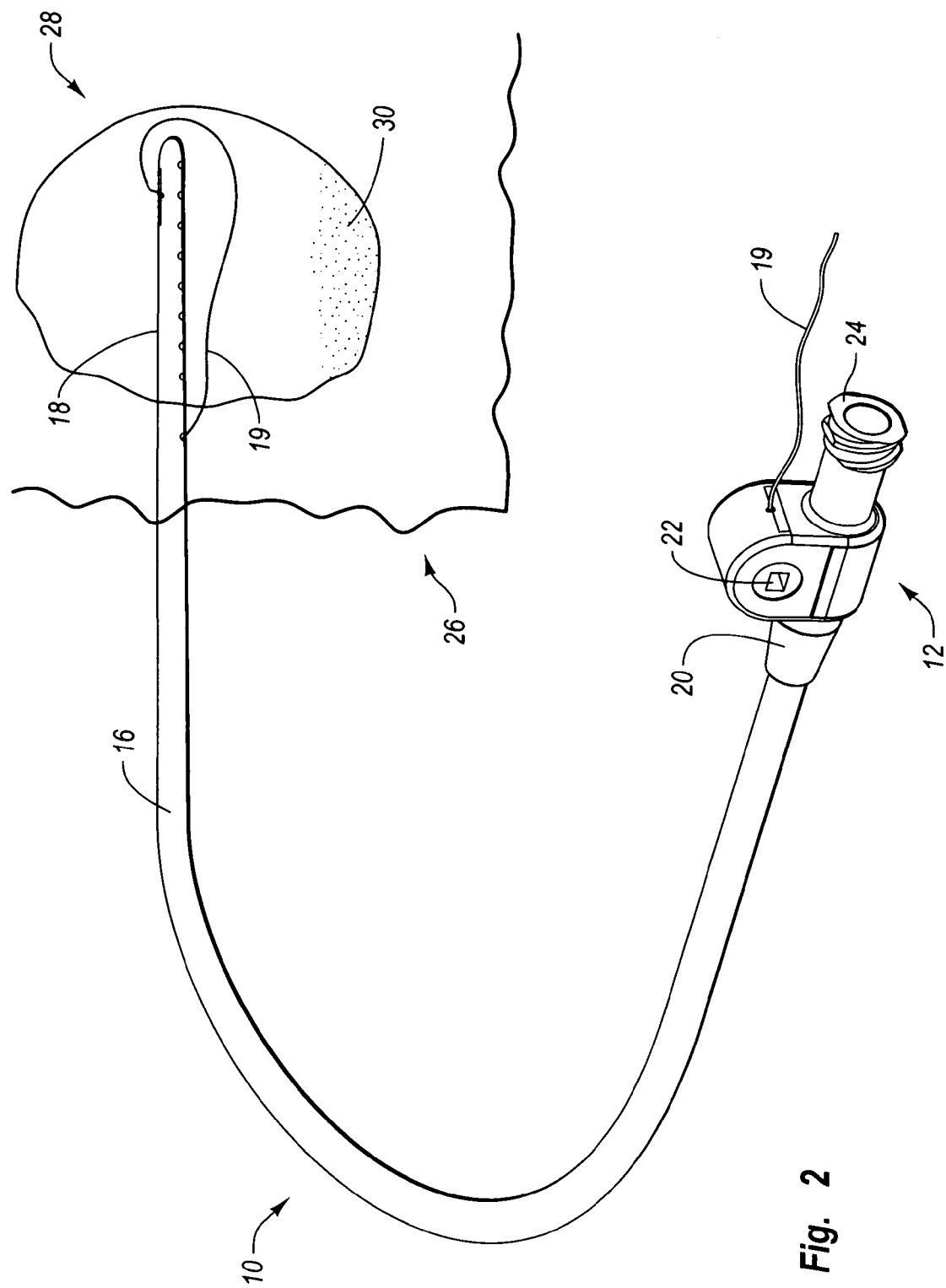
FIG. 2 is a perspective view of the drainage catheter of FIG. 1 being positioned in a volume of fluid to be drained within a patient in which the suture is in a released position.

FIG. 2 is a perspective view of the drainage catheter 10 of FIG. 1 during placement of distal end 18 of catheter tube 16 into a patient 26. In the illustrated embodiment, distal end 18 of catheter tube 16 has been introduced into a body cavity 28 of patient 26. A volume of bodily fluid 30 is positioned within body cavity 28. Distal end 18 of catheter tube 16 is in a released position allowing distal end 18 to be threaded in a substantially linear configuration to a desired position in body cavity 28 to allow proper drainage of bodily fluid 30.

In the illustrated embodiment, locking cam 22 is in a second position which allows free movement of suture 19. In the released configuration, suture 19 allows distal end 18 of catheter tube 16 to be straightened to allow proper introduction of distal end 18 of catheter tube 16 into a patient. The released configuration of suture 19 is depicted by the slack in suture 19. The slack in suture 19 is depicted for the sake of clarity and to more clearly illustrate operation of drainage catheter 10. In practice, during insertion, suture 19 will likely be positioned closely along the side of distal end 18 rather than in the loose configuration illustrated in FIG. 2.

The released position of locking cam 22 allows suture 19 to be manipulated by the user. For example, the user can reduce any slack in suture 19 by grasping the portion of suture 19 positioned proximally to hub 12 and pulling in a rearward direction. Before distal end 18 of catheter tube 16 is inserted into a patient, the user can manipulate distal end 18 or grasp the portion of suture 19 associated with distal end 18 to increase the slack in suture 19. This allows the user to fully straighten distal end 18 for insertion into the patient.

The straightened configuration of distal end 18 of catheter tube 16 allows catheter tube 16 to be inserted into a desired position within patient 26. In the illustrated embodiment, distal end 18 of catheter tube 16 has been inserted into a volume of bodily fluid 30 in a body cavity 28 of patient 26. Drainage catheter 10 is adapted to permit advantageous and efficacious draining of the volume of bodily fluid 30 in body cavity 28.

Figure 3:
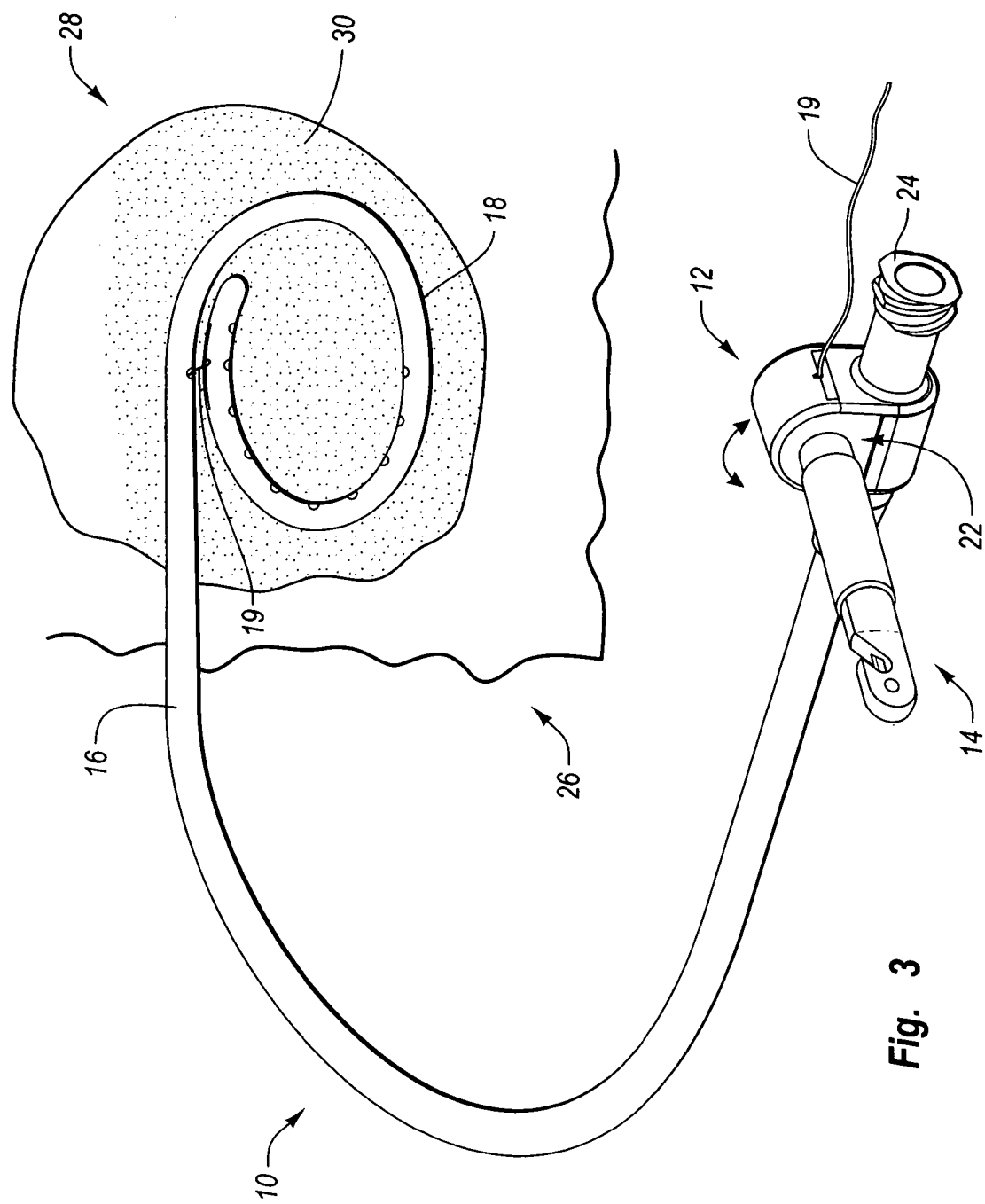
FIG. 3 is a perspective view of the drainage catheter of FIG. 1 in which the distal end of the drainage catheter is in an anchor configuration and the locking tool is being utilized with the locking cam.

FIG. 3 is a perspective view of the drainage catheter 10 in which the distal end 18 of the catheter tube 16 is in an anchor configuration and the locking tool 14 is being utilized with the locking cam 22. In the illustrated embodiment, the anchor configuration of distal end 18 comprises a pig tail-type loop. The pig tail-type loop configuration creates a sufficient cross section to inhibit retraction of distal end 18 of catheter tube 16 from patient 26.

In the illustrated embodiment, when distal end 18 of catheter tube 16 is advanced to the desired position, the user grasps and retracts the portion of suture 19 extending from catheter hub 12. This draws the tip of catheter tube 16 to the point from which suture 19 extends from the wall of catheter tube 16. Suture 19 extends from the wall of catheter tube 16 at a point proximal to the tip of catheter tube 16. As a result, when the tip of catheter tube 16 is drawn to proximal position on catheter tube 16 in which suture 19 extends from the wall of catheter tube 16, the distal end 18 of catheter tube 16 forms a pigtail-type loop. In the pigtail configuration, fluid can drain from the drainage bores formed on the inner circumference of the distal end 18 of catheter tube 16.

As will be appreciated by those skilled in the art, a variety of types and configurations of anchor configurations can be utilized without departing from the scope and spirit of the present invention. For example, in one embodiment an anchor having a bowtie configuration is utilized. In another embodiment, the cross-section of the distal end is expanded to provide an anchor configuration. In another embodiment, the distal end is bent, manipulated, or otherwise utilized to present a large cross-section relative to the entry site to provide anchoring of the distal end in a desired drainage position.

Locking tool 14 is shown inserted into locking cam 22 of hub 12. Locking tool 14 can be utilized to rotate locking cam 22 into a secured or released position. In the illustrated embodiment, locking tool 14 is shown rotating locking cam 22 to a secured position. In the secured position, the tension and/or positioning of suture 19 is fastened such that the tip of catheter tube 16 is secured to the side wall of catheter tube 16 at the exit point of suture 19. This maintains the anchor configuration of distal end 18 and the desired drainage positioning of distal end 18 in body cavity 28.

In the illustrated embodiment, the user can rotate locking tool 14 in either a clockwise or counterclockwise direction to move locking cam 22 from the released position to the secured position. This allows the user to secure suture 19 without having to ascertain a particular rotational direction required to move locking cam 22 to the secured position. This can be advantageous during the placement procedure where the practitioner's attention is often directed to other aspects of the procedure being performed. In another illustrative embodiment, one or more indicia are provided which enable the user to ascertain whether the locking cam 22 is in a secured position or a released position.

When the user desires to withdraw or reposition distal end 18 of drainage catheter tube 16 from patient 26, the user can use locking tool 14 to rotate locking cam to a released position. This allows suture 19 to be manipulated such that distal end 18 can be straightened and removed from the patient. When locking cam 22 is moved to a released position, tension on suture 19 is released allowing free movement of the tip of catheter tube 16 relative to the point where suture 19 exits sidewall of catheter tube 16. As the practitioner begins to withdraw catheter tube 16 from patient 26, the pigtail-type configuration of distal end 18 contacts the side of body cavity 28. Contact between distal end 18 and the side of body cavity 28 begins to straighten the pigtail loop allowing it to be safely and easily be withdrawn from the patient.

As will be appreciated by those skilled in the art, a variety of types and configurations of locking cams can be utilized without departing from the scope and spirit of the present invention. For example, in one embodiment the locking cam is rotated in a first direction to secure the suture and rotated in the opposite direction to release the suture. In another illustrative embodiment, the locking cam can be rotated alternatively between secured and released positions while being rotated in a single direction. In another embodiment, one or more indicia are provided to illustrate the direction of movement in which the locking cam should be rotated to secure or release the suture.

Figure 4:
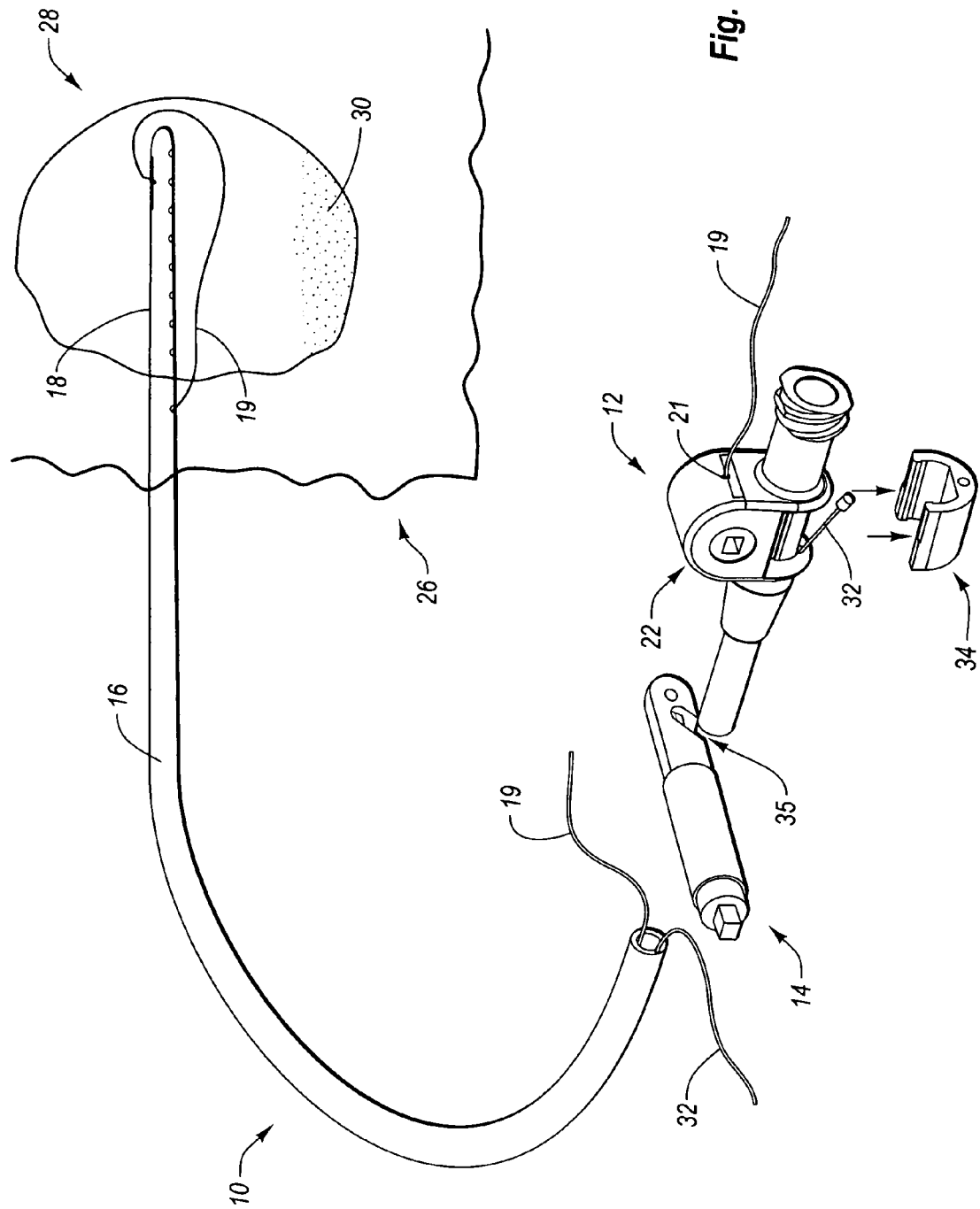
FIG. 4 is a perspective view of the drainage catheter of FIG. 1 in which the drainage catheter is being removed from the patient.

FIG. 4 is a perspective view of the drainage catheter of FIG. 1 in which the drainage catheter is being removed from the patient. This can be due to the fact that the drainage procedure is completed. Alternatively, removal of the catheter can be performed in order to reposition the distal end of the drainage catheter in a more optimal location in the patient. In the illustrated embodiment, the volume of bodily fluid 30 in body cavity 28 has been substantially drained. As a result, the practitioner is ready to remove drainage catheter 10 from patient 26. In the illustrated embodiment, a plurality of mechanisms for releasing the suture are depicted. As will be appreciated by those skilled in the art, in a typical procedure only one of the identified methods is utilized. However, the ability to utilize more than one mechanism provides additional flexibility and reliability in removing drainage catheter 10 from patient 26.

In the illustrated embodiment, locking cam 22 is depicted in the released position. In the released position, locking cam 22 allows movement of suture 19 such that distal end 18 can be straightened as the user begins to withdraw catheter tube 16 from patient 26. As distal end 18 begins to straighten and the tip of catheter tube 16 begins to move away from the point at which suture 19 exits the sidewall of catheter tube 16. During straightening of distal end 18, suture 19 is also pulled in a distal direction away from the point at which suture 19 exits the sidewall of catheter tube 16. A proximal portion of suture 19 extends from catheter hub 12 through a suture aperture 21. As distal end 18 straightens, the length of suture 19 extending proximally from catheter hub 12 shortens. This allows for straightening of distal end 18 permitting the removal of the catheter tube 16 through the entry channel of the catheter tube 16.

In the illustrated embodiment another mechanism is also provided for allowing release of the anchor configuration of distal end 18 of catheter tube 16. A stylet 32 and stylet release member 34 are provided in connection with drainage catheter 10. Stylet 32 and stylet release member 34 are shown separated from one another for the sake of clarity. As will be appreciated by those skilled in the art, sytlet 32 and stylet release member 34 are typically integrally coupled such that movement of stylet release member 34 results in movement of sytlet 32.

Stylet 32 runs from hub 12 to distal end 18 of catheter tube 16. Stylet 32 provides a securement apparatus for suture 19. A variety of types and configurations of mechanisms can be utilized for providing a stylet and suture combination with a drainage catheter. In the illustrated embodiment, stylet 32 is positioned in a secondary lumen positioned in the sidewall of catheter tube 16. By utilizing a secondary lumen, materials that are drained through the primary lumen of catheter tube 16 do not interfere with proper operation of stylet 32. Stylet 32 and the secondary lumen run from catheter hub 12 to the tip of the catheter tube 16. A small bore at the tip of catheter tube 16 exposes stylet 32 and allows suture 19 to be wrapped around stylet 32.

When the practitioner is ready to remove drainage catheter 10 from the patient, the practitioner disengages stylet release member 34 from its coupling with catheter hub 12. As the user pulls stylet release member 34 in the rearward direction, stylet 32 begins to be withdrawn from the secondary lumen of catheter tube 16. Once stylet 32 is sufficiently withdrawn, stylet 32 is also withdrawn from the position in which it is engaged by suture 19. Since suture 19 is solely secured to the tip of catheter tube 16 utilizing stylet 32, removal of stylet 32 results in release of suture 19 (not shown in FIG. 4.) When suture 19 is released, there is nothing to maintain the anchor configuration of distal end 18. As a result, as the user begins to withdraw distal end 18 from body cavity 28, distal end 18 can straighten and easily exit the entry channel of catheter tube 16. This can be particularly helpful in the event that materials in the lumen of catheter tube 16 have sufficiently encrusted suture 19 to prevent loosening or other manipulation of suture 19. Such encrustation can be experienced in biliary drainage procedures.

In the illustrated embodiment a third mechanism for releasing the anchor configuration of distal end 18 is also provided. In the embodiment, locking tool 14 includes a cutting blade 35. Cutting blade 35 is positioned in a recess of the locking tool in the end opposite the male engagement member. Cutting blade 35 is adapted to sever catheter tube 16 as is depicted. Severing catheter tube 16 releases engagement between the proximal portion and the distal portions of suture 19. The ability to completely severe catheter tube 16 can be desirable for the sake of convenience or in the event that suture 19 becomes encrusted or is otherwise difficult to manipulate within the tube. This can be particularly important in emergency or time-sensitive procedures.

As will be appreciated by those skilled in the art, a variety of types and configurations of release mechanisms can be utilized without departing from the scope and spirit of the present invention. For example, in one embodiment, a drainage catheter is utilized without a stylet and stylet release member. In another embodiment, a quick release mechanism is utilized with the locking cam to provide automatic release of the suture. In yet another embodiment, a cutting tool is provided that is a separate and additional tool from the locking tool. In another embodiment, the combination locking tool and cutting tool is secured by a lanyard or other mechansim to the catheter hub.

Figure 5:
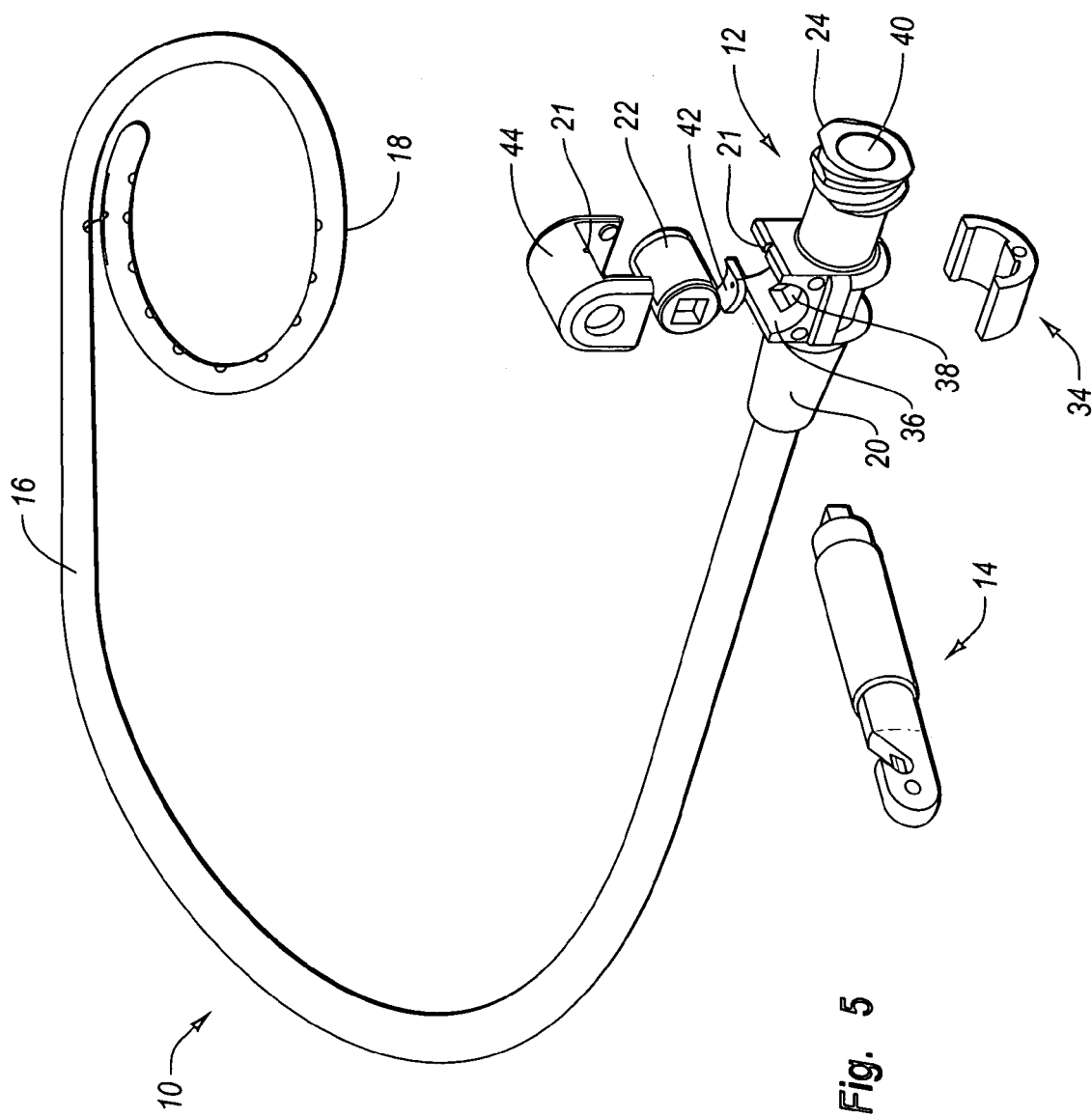
FIG. 5 is an exploded view of the drainage catheter of FIG. 1 illustrating the locking cam of the drainage catheter hub.

FIG. 5 is an exploded view of the drainage catheter of FIG. 1 illustrating the locking cam 22 of the catheter hub 12. In the illustrated embodiment, catheter hub 12 includes a locking cam 22, locking cam seat 36, a seal seat 38, a main lumen 40, a seal 42, and a locking cam housing 44. Locking cam 22 is a cylindrically shaped member that is adapted to be housed between locking cam seat 36 and locking cam housing 44. Locking cam 22 is adapted to rotate within locking cam seat 36 and locking cam housing 44 such that the outer diameter of locking cam 22 is positioned adjacent the inner diameter of locking cam seat 36 to cooperatively engage suture 19 (not shown) when locking cam 22 is in the secured position.

Locking cam seat 36 provides a stable base having an inner diameter closely approximating the cross section of locking cam 22. Locking cam housing 44 is positioned over locking cam 22 to secure the position of locking cam relative to locking cam seat 36. Locking cam housing 44 is secured to locking cam seat 36 to maintain the correct juxtaposition of locking cam 22 relative to locking cam seat 36. In the illustrated embodiment, locking cam housing 44 includes an aperture to allow access to the female member of locking cam 22. This permits the user to rotate locking cam 22 between the secured position and the released position. Locking cam housing 44 also includes a suture aperture 21 for allowing suture 19 (not shown) to pass to the exterior of catheter hub 12. In the illustrated embodiment, locking cam comprises a camming means for selectively providing release and securement of the suture to maintain or release the anchor configuration of the distal end of the catheter. In the illustrated embodiment, the locking cam seat comprises a means for cooperatively engaging the camming means to provide cooperative engagement of the suture when the camming means is in a secured position.

Seal 42 is positioned below locking cam 22 in seal seat 38. Suture 19 is threaded through a suture channel in the middle of seal 42. Seal 42 allows suture 19 to pass from main lumen 40 of catheter hub 12 to the space between locking cam 22 and locking cam seat 36 without allowing the passage of bodily fluids that are draining through main lumen 40. In the illustrated embodiment, seal 42 is comprised of silicone. In another embodiment, the seal is comprised of thermoplastic gel material, rubber, latex, neoprene, isoprene, or other suitable sealing material.

As will be appreciated by those skilled in the art, a variety of types and configurations of catheter hubs can be utilized without departing from the scope and spirit of the present invention. For example, in one embodiment the locking cam seat and the locking cam housing are integrally coupled to one another. In another embodiment, the suture passes between the locking cam and the locking cam housing to secure the suture.

FIG. 6 is a cross-sectional view of the catheter hub 12 and catheter tube 16 illustrating the juxtaposition to the suture 19 relative to other components of the drainage catheter. In the illustrated embodiment, catheter tube 16 is coupled to catheter hub 12 utilizing catheter tube coupler 20. The coupling of catheter hub 12 to catheter tube 16 positions a catheter lumen 46 of catheter tube 16 in fluid communication with a main lumen 40 of catheter hub 12. This allows bodily fluids to be drained from the patient, to the catheter lumen 46 and then to the main lumen 40 of catheter hub 12 before leaving the drainage catheter 10.

Suture 19 is threaded along the length of catheter lumen 46 and into main lumen 40. However, as suture 19 passes through catheter lumen 46 it exits main lumen 40 through seal seat 38. From seal seat 38, suture 19 is threaded along the surface of locking cam seat 36 before exiting the aperture in locking cam housing 44 (not shown). The pathway of suture 19 provides both an effective conduit for suture 19 to the tip of catheter tube 16 while providing simple and effective manipulation of suture 19. Additionally, the juxtaposition of suture 19 and the components of catheter hub 12 allow a user to simply and efficiently secure the position of suture 19. By being able to secure and release the position of suture 19 the user can secure or release the anchor configuration of the distal end of the catheter tube to position or remove the catheter from the patient.

Stylet release member 34 is shown separated from the other components of catheter hub 12. Retracting stylet release member 34 in a rearward direction pulls stylet 32 in a rearward direction as well. Once stylet 32 is retracted sufficiently in a rearward direction, suture 19 is no longer secured to the distal end 18 (not shown) of catheter tube 16 and the anchor configuration of the distal end 18 (not shown) is released. Stylet 32 extends from catheter hub 12 to a stylet side lumen 50 positioned in the wall of catheter tube 16. Stylet side lumen 50 allows for operation of stylet 32 without interference from suture 19 or articles and materials being drained through catheter lumen 46 of catheter tube 16.

FIG. 7A and FIG. 7B illustrate locking cam 22 and the components of locking cam 22 utilized to release and secure the suture (not shown) utilized in connection with the drainage catheter. In the illustrated embodiment, locking cam 22 includes a female member 52 and a tapered camming surface 54. Female member 52 comprises a square shaped void positioned in the side face of locking cam 22. Female member 52 is adapted to accommodate a male member of locking tool 14 (not shown) to allow a user to rotate locking cam 22. As will be appreciated by those skilled in the art, a variety of types and configurations of mechanisms for causing rotation of the locking cam can be utilized without departing from the scope and spirit of the present invention. For example, in one embodiment a female member having a hexagonal configuration can be utilized. In another embodiment, a male member that can be twisted using the user's fingers or mechanism for rotating the locking cam is provided.

Tapered camming surface 54 includes a release portion 58 and a securement portion 56. The tapered camming surface 54 extends inwardly from the outside diameter of the locking cam such that the release portion of the tapered camming surface 54 has a greater displacement from the inner contact surface of the seat (not shown) than the securement portion. When the locking cam 22 is rotated such that the suture is located between the release portion 58 and the inner contact surface of the seat (not shown) the suture can be moved by the user. When the locking cam 22 is rotated such that the suture is located between the securement portion 56 and the inner contact surface, the suture is cooperatively engaged between the inner contact surface and the securement portion 56 to prevent movement of the suture. In the embodiment illustrated in FIG. 7B securement portions 56 are positioned on both sides of release portion 58.

As will be appreciated by those skilled in the art, a variety of types and configurations of locking cams and tapered camming surfaces can be utilized without departing from the scope and spirit of the present invention. For example, in one embodiment, the entire outer surface is covered with alternating securement portions and release portions such that the locking cam can be rotated continuously while providing alternating locking and releasing of the suture. In another embodiment, the suture is secured using a surface other than the tapered camming surface. In yet another embodiment, a movable member other than the locking cam is provided to secure the suture.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the drainage catheter comprising:

a catheter tube having a proximal end and a distal end, the distal end of the catheter tube being configured to be positioned in tissue, cavity, or other location within the body of the patient having an amount of fluid to be drained;

a suture running the length of at least a portion of the catheter tube and being secured to the distal end of the catheter tube to selectively maintain the anchor configuration of the distal end of the catheter;

a catheter hub coupled to the proximal end of the catheter tube, the catheter hub comprising:

a seat having an inner contact surface and adapted to be in contact with a portion of the suture;

a locking cam adapted to be positioned in the seat, the locking cam having an outside diameter adapted to conform to the inner contact surface of the seat to provide rotational movement of the locking cam relative to the seat such that the outside diameter of the locking cam remains in contact with the seat around substantially the entire outside diameter of the locking cam; the locking cam having a tapered camming surface positioned on a portion of the outside diameter of the locking cam such that the tapered camming surface is utilized to cooperatively engage a portion of the suture inside the catheter hub along a substantial length of the inner contact surface of the seat to selectively secure the suture based on the rotational position of the locking cam, wherein the tapered camming surface comprises;

a release portion, the release portion being positioned at a given radial position on an outer surface of the locking cam, the release portion extending inwardly from the outside diameter of the locking cam such that the release portion has a predetermined amount of displacement from the inner contact surface of the seat, wherein when the locking cam is rotated to a first rotational position the portion of the suture positioned inside the hub is positioned between the release portion and the inner contact surface of the seat, the release portion providing a sufficient amount of clearance between the release portion and the inner contact surface of the seat to allow the suture to be moved by the user relative to the locking cam and the seat; and a securement portion, the securement portion being positioned at a given radial position on the outer surface of the barrel, the securement portion having a lesser amount of displacement from the inner contact surface of the seat than the release portion, such that when the locking cam is rotated to a second position, the portion of the suture positioned inside the hub is cooperatively engaged between the securement portion of the camming surface and the inner contact surface of the seat to control movement of the suture relative to the locking cam and the seat.

2. The drainage catheter of claim 1, wherein the locking cam is configured to allow the user to selectively secure the suture to maintain the anchor configuration of the distal end of the catheter.

3. The drainage catheter of claim 1, wherein the securement portion of the camming surface is positioned to one side of the release portion of the tapered camming surface.

4. The drainage catheter of claim 3, wherein a second securement portion is positioned on the opposite side of the release portion such that rotation of the locking cam in either a clockwise or counter clockwise direction moves the locking cam from a released position to a securement position.

5. The drainage catheter of claim 1, wherein the locking cam is configured to be utilized in connection with a locking tool.

6. The drainage catheter of claim 5, wherein the locking tool is utilized to rotate the locking cam between the released position and the securement position.

7. The drainage catheter of claim 6, wherein the locking cam and locking tool are cooperatively engaged in a male/female configuration.

8. The drainage catheter of claim 7, wherein the locking cam includes a female member and the locking tool includes a male member.

9. A drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the drainage catheter comprising:
a catheter tube having a proximal end and a distal end, the distal end of the catheter tube being configured to be positioned in tissue, cavity, or other location within the body of the patient having an amount of fluid to be drained;
a suture running the length of the catheter tube and being secured to the distal end of the catheter tube to selectively maintain the anchor configuration of the distal end of the catheter;
a catheter hub coupled to the proximal end of the catheter tube, the catheter hub having an inner contact surface and a locking cam adapted to allow the user to selectively secure the suture to maintain the anchor configuration of the distal end of the catheter, wherein a portion of the suture inside the catheter hub is positioned between the exterior of the locking cam and the inner contact surface, and wherein the locking cam is rotatable to a first position to permit movement of the suture and to a second position to secure the suture, the locking cam having a release portion and a securement portion, the release portion being positioned at a given radial position on an outer surface of the locking cam, the release portion extending inwardly from the outside diameter of the locking cam such that the release portion has a predetermined amount of displacement from the inner contact surface of the seat, wherein when the locking cam is rotated to the first rotational position the portion of the suture positioned inside the hub is positioned between the release portion and the inner contact surface of the seat, the release portion providing a sufficient amount of clearance between the release portion and the inner contact surface of the seat to allow the suture to be moved by the user relative to the locking cam and the seat and the securement portion being positioned at a given radial position on the outer surface of the barrel, the securement portion having a lesser amount of displacement from the inner contact surface of the seat than the release portion, such that when the locking cam is rotated to the second position, the portion of the suture positioned inside the hub is cooperatively engaged between the securement portion and the inner contact surface of the seat to control movement of the suture relative to the locking cam and the seat.

10. The drainage catheter of claim 9, further comprising a locking tool for rotating the locking cam between the first position and the second position.

11. The drainage catheter of claim 10, wherein the locking tool includes a cutting member for severing one or both of the suture and the catheter tube to release the anchor configuration of the distal end of the catheter tube.

12. The drainage catheter of claim 11, wherein the cutting member is positioned on locking tool opposite an end of the locking tool utilized to rotate the locking cam between the first position and the second position.

13. The drainage catheter of claim 12, wherein the cutting member comprises a cutting blade.

14. The drainage catheter of claim 9, further comprising a stylet configured to selectively secure the suture relative to the tip of catheter tube to maintain the anchor configuration of the distal end of the catheter tube.

15. The drainage catheter of claim 14, further comprising a stylet release member linked to the stylet allowing the stylet to be utilized to release the anchor configuration of the distal end of the catheter tube.

16. The drainage catheter of claim 15, wherein the stylet release member is secured to the stylet such that the stylet can be retracted in a rearward direction within the catheter tube effectuating release of the suture.

17. The drainage catheter of claim 9, wherein one of a plurality of mechanisms are provided to release the anchor configuration of the distal end of the catheter tube.

18. The drainage catheter of claim 17, wherein the one of a plurality of mechanisms comprise one or more of a stylet, a locking cam, and a cutting member.

19. A drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the drainage catheter comprising:
a catheter tube having a proximal end and a distal end, the distal end of the catheter tube being configured to be positioned in tissue, cavity, or other location within the body of the patient having an amount of fluid to be drained;
a suture running the length of the catheter tube and being secured to the distal end of the catheter tube to selectively maintain the anchor configuration of the distal end of the catheter;
a catheter hub coupled to the proximal end of the catheter tube, the catheter hub having an inner contact surface and a locking cam adapted to allow the user to selectively secure the suture to maintain the anchor configuration of the distal end of the catheter, wherein the locking cam includes a tapered camming surface having a securement portion for securing a portion of the suture inside the catheter hub between the exterior of the tapered camming surface and the inner contact surface and a release portion for allowing movement of the suture around the exterior of the tapered camming surface, the release portion being positioned at a given radial position on an outer surface of the locking cam, the release portion extending inwardly from the outside diameter of the locking cam such that the release portion has a predetermined amount of displacement from the inner contact surface of the seat, wherein when the locking cam is rotated to the first rotational position the portion of the suture positioned inside the hub is positioned between the release portion and the inner contact surface of the seat and the securement portion being positioned at a given radial position on the outer surface of the barrel, the securement portion having a lesser amount of displacement from the inner contact surface of the seat than the release portion, such that when the locking cam is rotated to the second position, the portion of the suture positioned inside the hub is cooperatively engaged between the securement portion and the inner contact surface of the seat to control movement of the suture relative to the locking cam and the seat.

20. The drainage catheter of claim 19, further comprising a locking cam seat adapted to accommodate the locking cam.

21. The drainage catheter of claim 20, wherein the suture is adapted to be positioned between the tapered camming surface and the locking cam seat.

22. The drainage catheter of claim 21, wherein the suture is adapted to be cooperatively engaged between the securement portion of the tapered camming surface and the locking cam seat to prevent movement of the suture.

23. The drainage catheter of claim 19, further comprising one or a plurality of indicia for indicating whether the locking cam is in a released position or a secured position.

24. The drainage catheter of claim 23, further comprising one or a plurality of indicia for indicating the direction of movement for moving between a secured position and a released position.

25. The drainage catheter of claim 19, wherein the tapered camming surface includes a plurality of securement portions.

26. The drainage catheter of claim 25, wherein the tapered camming surface includes a plurality of release portions.

27. A drainage catheter hub for use with a drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the drainage catheter hub comprising:
   a body having a main lumen and a connector for securing the body to a catheter tube;
   a locking cam adapted to allow the user to selectively secure the suture to maintain the anchor configuration of the distal end of the catheter, wherein the locking cam includes a tapered camming surface having a securement portion and a release portion;
   a locking cam seat having a inner surface accommodating the locking cam, wherein the suture is positioned on the exterior of the locking cam between the tapered camming surface and the locking cam seat, wherein the securement portion has a lesser amount of displacement from the inner contact surface of the seat than the release portion such that the securement portion of the tapered camming surface and the locking cam seat cooperatively engage the suture when the locking cam is rotated to a securement position, and wherein when the release portion is positioned at a given radial position on an outer surface of the locking cam, the release portion extends inwardly from the outside diameter of the locking cam such that the release portion has a predetermined amount of displacement from the inner contact surface of the seat providing a sufficient amount of clearance between the release portion and the inner contact surface of the seat to allow the suture to be moved by the user relative to the locking cam and the seat when the locking cam is rotated to the release position.

28. The drainage catheter of claim 27, wherein the release portion of the tapered camming surface extends inwardly from the outside diameter less than the securement portion of the tapered camming surface.

29. A drainage catheter hub for use with a drainage catheter tube which provides a fluid pathway for draining bodily fluid from a cavity or tissue of a patient, the drainage catheter being configured such that a suture utilized in connection with the drainage catheter selectively secures the distal end of the catheter in an anchor configuration, the catheter hub configured to be coupled to the proximal end of the catheter tube, the drainage catheter hub comprising:
   a seat having an inside diameter, the inside diameter forming a substantially circular inner contact surface, the inner contact surface adapted to be in contact with a length of the suture;
   a locking cam, comprising a cylindrically shaped member adapted to be positioned in the seat, the locking cam having:
      an outside diameter, the outside diameter forming a substantially circular contact surface, the outside diameter configured to remain in contact with substantially the entire diameter of the substantially circular inner contact surface of the seat such that the outside diameter of the locking cam is in contact with the substantially circular inner contact surface of the seat throughout the range of rotation of the locking cam wherein the contact between the substantially circular inner contact surface of the seat and the substantially circular outside diameter of the locking cam provides the sliding surface rotation of the locking cam relative to the other components of the drainage catheter hub and wherein a portion of the suture positioned inside the catheter hub is positioned between the locking cam and a substantial portion of the contact surface of the seat; and
      a tapered camming surface positioned on a portion of the outside diameter of the locking cam such that, the tapered camming surface is utilize to cooperatively engage the suture along a substantial length of the inner contact surface of the seat to selectively secure the suture based on the rotational position of the locking cam, wherein the tapered camming surface comprises;
         a release portion, the release portion being positioned at a given radial position on an outer surface of the locking cam, the release portion extending inwardly from the outside diameter of the locking cam such that the release portion has a predetermined amount of displacement from the inner contact surface of the seat, wherein when the locking cam is rotated to a first rotational position the portion of the suture positioned inside the hub is positioned between the release portion and the inner contact surface of the seat, the release portion providing a sufficient amount of clearance between the release portion and the inner contact surface of the seat to allow the suture to be moved by the user relative to the locking cam and the seat; and
         a securement portion, the securement portion being positioned at a given radial position on the outer surface of the barrel, the securement portion having a lesser amount of displacement from the inner contact surface of the seat than the release portion, wherein when the locking cam is rotated to a second position the portion of the suture positioned inside the hub is cooperatively engaged between the securement portion of the camming surface and the inner contact surface of the seat to control movement of the suture relative to the locking cam and the seat; and a mechanism to rotate the locking cam between the first rotational position and the second rotational position to secure or allow movement of the suture relative to the catheter hub.

* * * * *

UNITED STATES PATENT AND TRADEMARK OFFICE
CERTIFICATE OF CORRECTION

PATENT NO. : 7,641,630 B2 Page 1 of 1
APPLICATION NO. : 11/078140
DATED : January 5, 2010
INVENTOR(S) : Accisano, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1028 days.

Signed and Sealed this

Sixteenth Day of November, 2010

David J. Kappos
*Director of the United States Patent and Trademark Office*